United States Patent [19]

Cummings et al.

[11] 3,930,957
[45] Jan. 6, 1976

[54] APPARATUS AND METHOD FOR BIOLOGICAL ANALYSIS

[75] Inventors: John P. Cummings, Bloomington, Minn.; Robert B. Koch, Starkville, Miss.

[73] Assignee: Honeywell Inc., Minneapolis, Minn.

[22] Filed: July 11, 1974

[21] Appl. No.: 487,706

[52] U.S. Cl. ........................................ 195/103.5 R
[51] Int. Cl.$^2$ ........................................ C12K 1/04
[58] Field of Search ........................... 195/103.5 R

[56] References Cited
UNITED STATES PATENTS

| | | | |
|---|---|---|---|
| 3,427,225 | 2/1969 | Harvill et al. ................ | 195/103.5 R |
| 3,635,681 | 1/1972 | Rogers ......................... | 195/103.5 R |
| 3,838,011 | 9/1974 | Hagen et al. ................. | 195/103.5 R |
| 3,839,154 | 10/1974 | Messing ....................... | 195/63 |

*Primary Examiner*—A. Louis Monacell
*Assistant Examiner*—C. A. Fan
*Attorney, Agent, or Firm*—Charles G. Mersereau; Henry L. Hanson

[57] ABSTRACT

A continuous method and apparatus for the determination of urea in a biological fluid such as blood, for example, is disclosed. In a continuously flowing system, the biological sample is introduced into a buffered carrier solution of low electrical conductance and is caused to flow into a chamber containing an immobilized enzyme which catalyzes a specific reaction which changes the electrical properties of the solution by increasing the dissociated ion concentration therein. This increase in dissociated ion concentration is directly proportional to the original concentration of urea in the biological sample; and any one of the several conventional electrical measurements may be made to determine the increase in such concentration or the rate of increase in such concentration and thereby determine the concentration of urea in the original biological sample. The buffered carrier solution containing the products of the enzyme-catalyzed reaction is reclaimed by circulating it through a deionization, purification stage in which the solution conductivity is substantially returned to the prereaction value. The carrier solution is recirculated and used for processing additional samples. The enzyme, urease, is immobilized in a manner which allows many tests to be run without any significant loss thereof. The savings in enzyme requirements and the savings accomplished by recirculating the buffered carrier solution greatly reduces the cost of analysis.

10 Claims, 2 Drawing Figures

APPARATUS AND METHOD FOR BIOLOGICAL ANALYSIS

BACKGROUND OF THE INVENTION

1. Field of the Invention

The present invention relates generally to the field of testing samples of biological fluids for specific components therein, and, more particularly, to the quantitative determination of urea in a biological fluid such as blood based on a urease-catalyzed reaction in an organic buffer carrier solution.

2. Description of the Prior Art

The use of enzymes to aid in the determination of the concentration of various components in biological fluid is gaining rapidly as a simpler, extremely specific and more precise approach to the solution of sensing the concentration of one or more products, depletion of one or more reactants or other changes in the solution characteristics following an enzyme-catalyzed reaction in which a specific enzyme is utilized to catalyze a known reaction involving a component of interest in a fluid biological sample. One important and commonly used test involves the determination of the concentration of urea in blood serum. The level in blood serum has been found to be significant in evaluating the normality of the operation of the kidneys.

In the past a great many analytical techniques have been utilized for the analysis of biological fluids including those involving enzyme-catalyzed reactions, the results of which depend upon colorimetric techniques. These have proved to be highly susceptible to interferences or disturbances which may adversely affect the accuracy of the results. Such techniques normally rely on the action of a strong oxidizing agent or reducing agent upon the products of the enzyme-catalyzed reaction to produce a colorsensitive endpoint. These reagents, however, are generally not selective in their action on any oxidizable or reducible species and other impurities in the solution may dramatically affect the intensity of the color produced or cause a spectral shift therein which results, of course, in an inaccurate determination.

More recently, a method has been developed for the measurement of blood urea nitrogen (BUN) based on solution conductivity. It has been found that urea, which is a nonionic species, reacts with the enzyme urease to produce ionic charge carriers in an amount proportional to the original concentration of urea in the sample. The reaction may be described as follows:

$$NH_2CONH_2 + H_2O \xrightarrow{\text{urease}} CO_3^{-2} + 2NH_4^+$$

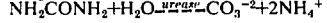

As can readily be seen from the above, the concentration of the reaction product, if sufficiently dilute, as in the biological samples tested, the hydrolysis to ammonium and carbonate ions is substantially complete and three charge carriers are produced for each molecule of urea reacted. This drastic increase in the number of charge carriers caused by the above reaction can be measured by conventional electrical techniques such electrical measurement is directly related to the concentration of urea in the biological specimen.

One prior art device which utilizes this basic principle can be found in U.S. Pat. No. 3,765,841 to Paulson et al, which illustrates and describes an apparatus for determining the concentration of, inter alia, urea in biological fluids by measuring the rate of change in conductivity of the reacting solution during a predetermined, fixed time interval in a strictly batch-type process. By that invention, a biological sample is introduced into a carrier solution along with a quantity of the enzyme urease in a free state and the rate of change of conductivity of the solution is measured after a fixed interval in which the initial portion of the reaction takes place. Because the initial stage of the reaction proceeds quite rapidly and any rate of change of conductivity measurement during the initial part of the reaction is almost infinite, the system must have an intricate built in electrical delay to allow for this initial phase to be completed prior to the measurement of the rate of change of conductivity produced by the reaction. Also, that instrument possesses all of the drawbacks inherent to a batch analyzer. Thus, after each sample is reacted and measured, both the carrier solution in which the reaction takes place and the quantity of enzyme which is utilized to catalyze the reaction are discarded. This greatly increases the cost associated with the processing of each sample.

SUMMARY OF THE INVENTION

According to the present invention, there is provided a method and apparatus for chemical analysis of biological samples, generally, and in particular, for the determination of urea in such samples. The present invention retains the desirability of utilizing electrical measurements in the determination and eliminates the drawbacks associated with the requirement of allowing for a large, instantaneous change in the characteristic of the solution produced by the initial phase of the reaction and the requirement of providing a fresh carrier solution and enzyme for each sample to be tested. The present method and apparatus utilizes a recirculating flow-through system in which the carrier solution may be recycled and utilized for testing a plurality of samples and in which the enzyme is immobilized in a manner which allows free contact between the solution components and the enzyme with little or no loss of enzyme occasioned thereby thus allowing repeated use of the same enzyme material.

By means of the present invention there is provided a continuous flow method and apparatus for the enzymatic determination of urea in biological serum samples which utilizes reusable, immobilized enzyme and reclaimable, recirculated substantially non-ionic organic buffered carrier solution to maintain the desired solution pH. In the preferred embodiment, the organic buffer solution continuously circulates through a first chamber, which may be in an enclosed column containing an appropriate amount of the enzyme urease immobilized in a cross-linked polyacrylamide gel in a manner which substantially prevents leaching of the enzyme yet allows free contact between the carrier solution and the entrapped enzyme molecules. A sample is normally introduced into the carrier solution upstream of this enzyme-containing chamber and the catalyzed reaction takes substantially within that chamber. The carrier solution containing the substantially reacted urea proceeds to a second chamber wherein an electrical conductivity measurement may be made. The reacted and measured solution then proceeds into a third chamber for chemical reclamation of the buffered carrier solution containing, for example, a conventional ion exchange bed which removes substantially all the electroactive ionic species therefrom substantially returning the solution conductivity to the value before the reaction. The buffered organic buffer carrier solution is then recirculated to the system and may be reused in the measurement of subsequent samples.

Of course, as soon as a given sample has passed through the enzyme containing chamber a subsequent sample may be introduced into the system without disturbing the results of either test. The sample size associated with this system may be readily controlled by injecting a given amount of sample into the system and the flowrate may conveniently controlled e.g., in a gravity-flow system, by the size and length of the various conduit and chamber components of the flow system such that the sample is substantially reacted by the time the solution reaches the second chamber. The recirculating system may be one utilizing a pump to recirculate the reclaimed carrier solution into a reservoir containing a large amount of the carrier solution. A constant-head pump may also be utilized to maintain the same flowrate throughout the system. In this manner, many samples may be run before the buffer carrier solution must be changed.

The organic buffer carrier solution is one which is compatable with the urea-containing biological fluid samples to be tested, the immobilized enzyme and one which does not affect or interfere with the desired enzyme-catalyzed reaction. An example of such a combination is an aqueous solution of 0.05M Tris (Hydroxymethyl) aminomethane adjusted to pH 7 by the addition of glycine.

The present invention contemplates measuring the increase in solution conductivity which is a measurement of the initial urea concentration in a sample by any of several techniques including:

1. Utilizing a single conductance cell in the second chamber to measure the value of the conductance after the reaction is substantially completed.

2. Utilizing a differential method in which two conductant cells are used, one placed before and one after the sample enters the enzyme-containing chamber to measure the increase in conductance occasioned by the reaction.

3. A differential method in which one conductance cell is placed within the enzyme-containing chamber to measure the time rate of production of charge carriers at a point where such is proportional to the initial concentration of urea in the solution.

Thus, there is contemplated by the present invention a recirculating continuous-flow system which obtains maximum utilization of both the organic buffer carrier and the enzyme.

DESCRIPTION OF THE PREFERRED EMBODIMENT

Figure 1:
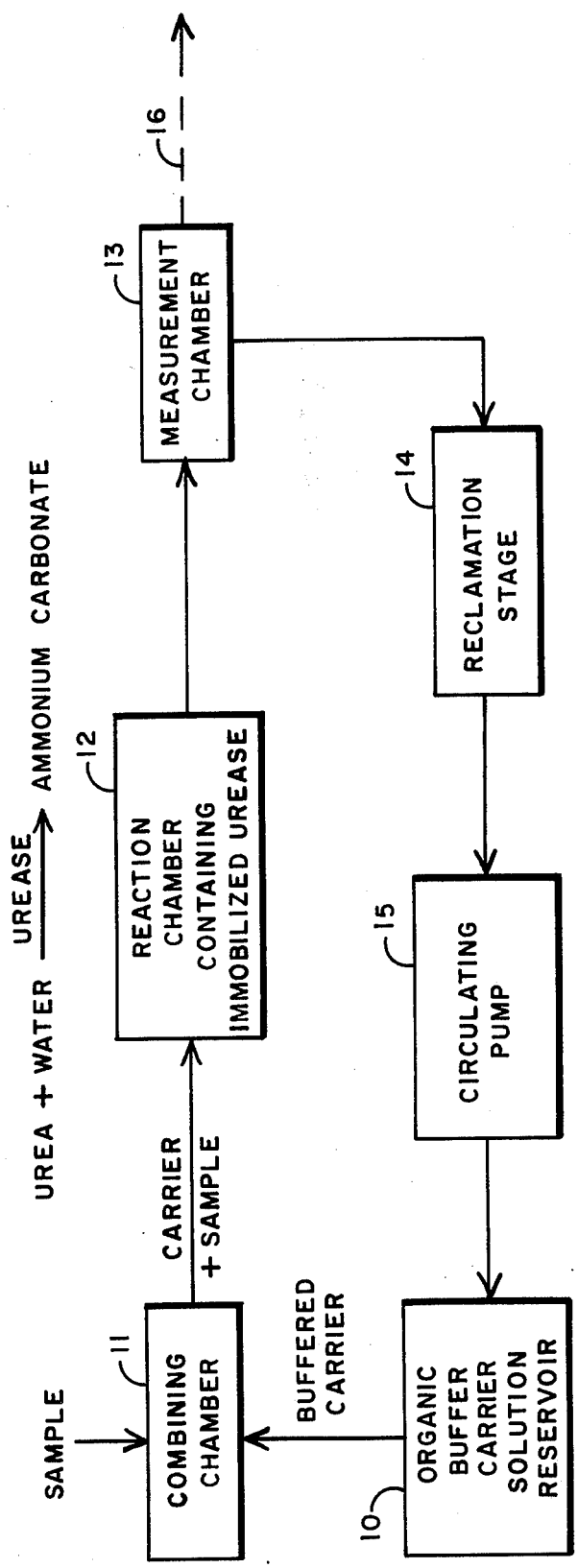
FIG. 1 is a schematic representation of the flow system of the apparatus of the invention.

FIG. 1 represents a schematic flow diagram illustrating the preferred embodiment of the invention. An organic buffer carrier solution, in which the reaction takes place and also which serves as a cleansing solution for the analysis system, is supplied continuously from a reservoir 10 into a chamber 11 where it is combined with the biological sample to be analyzed. The carrier solution, combined with the sample then flows into a packed column reaction chamber 12 containing an amount of immobilized urease which catalyzes the reaction in which the non-ionic urea is transformed into ammonium carbonate in the dissociated form of ammonium and carbonate ions. The reacted solution then flows into a measurement chamber 13 wherein the electrical conductance of the substantially reacted solution is measured. The reacted solution is then recirculated through a reclamation chamber 14 wherein the carrier is substantially de-ionized so that it may be reused in the analysis of further samples. The substantially electrically inactive reclaimed solution is then recirculated as by circulating pump 15 returning to the reservoir 10. Periodically, the organic buffer carrier solution may be changed by allowing the used solution to drain out of the system through a drain shown at 16. Continuous circulation of the organic buffer carrier solution insures that the reaction and measurement chambers will be cleansed of the previous samples prior to the introduction of a new sample.

Figure 2:
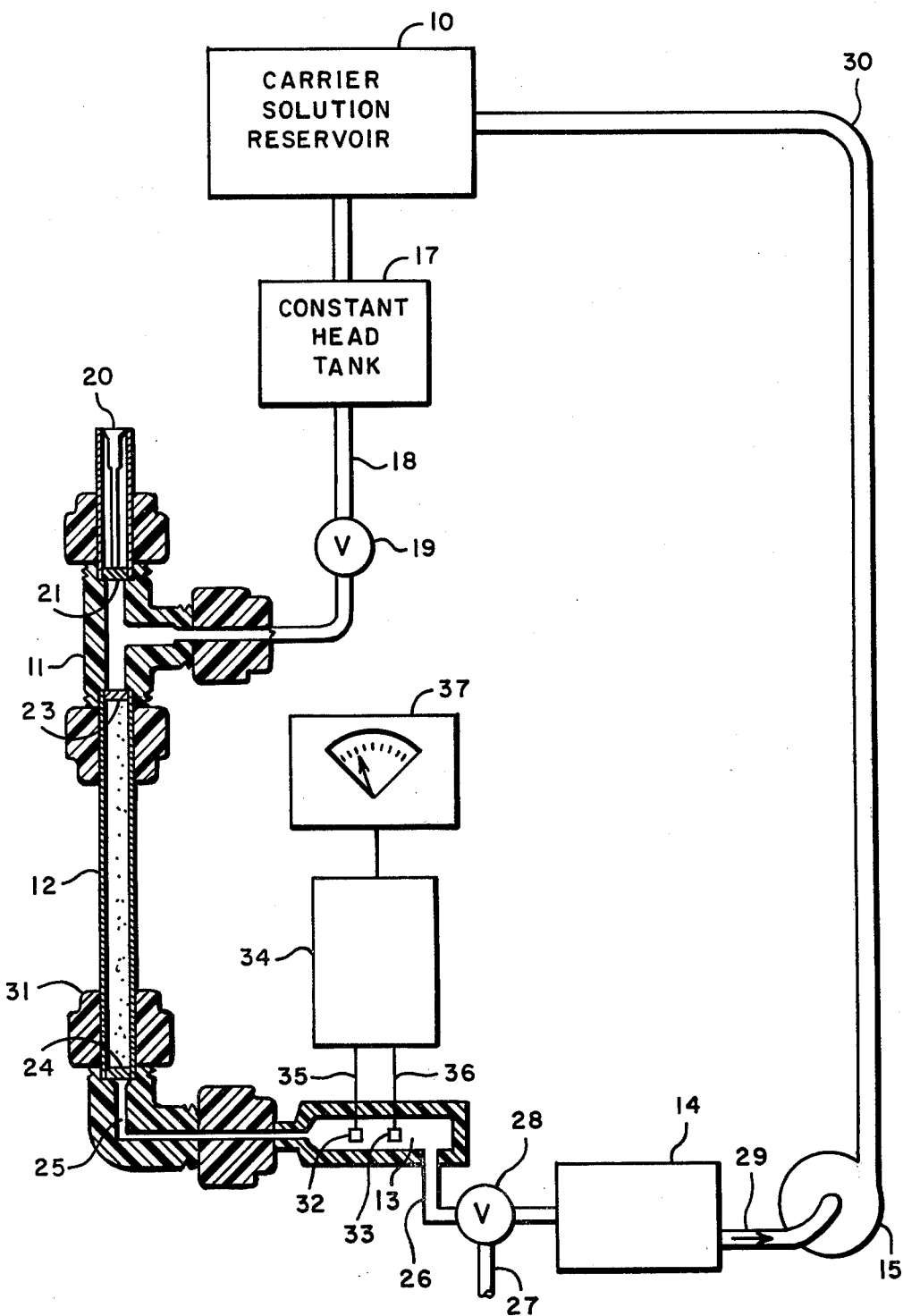
FIG. 2 is an illustration, partly in diagramatic form and partly in section, depicting one embodiment of the apparatus of the invention.

Turning now to FIG. 2 there is illustrated a typical apparatus for carrying out the process of the invention. For purposes of clarity some of the figure is shown in section and, for simplification, some conventional parts are shown in block form. The reservoir 10 for the buffered organic carrier solution may be used in the gravity-feed type arrangement wherein the reservoir supplies a constant head tank overflow weir system shown in block form at 17. The carrier solution is then supplied through a conduit 18, having a flow shut off valve 19, at a constant rate into the combining chamber 11. The measured sample of biological fluid to be analyzed is introduced into the system from a separate injection port 20. This may be done by utilizing a graduated syringe or other pre-measured small volume container. The bottom of the injection port may be closed as by a septum 21 and the sample injected therethrough into the chamber 11. The sample then combines with the carrier solution in the chamber 11 prior to entering into the reaction column 12.

The combined solution passes through a porous plug 23, which may be a fine metal screen (approximately 100 mesh) or a glass frit material of similar permeability. Reaction column 12 contains an amount of the enzyme urease immobilized in a finely divide gel matrix. A second porous plug 24, substantially identical to the plug 23, closes the bottom of the column and, while allowing free flow of the test solution therethrough prevents any loss of the enzyme-containing gel from the column. After flowing through the column 12, the test solution flows via conduit 25 into the measurement chamber 13 where the final conductance measurement is made in a manner discussed in greater detail below.

The effluent or reacted solution flows from chamber 13 into a reclamation chamber 14 as by means of a conduit 26. The electrically active ionic species are substantially removed or neutralized therein in a manner discussed below. A drain opening 27 located in conduit 26 may be utilized to drain the system when desired as by utilizing a three way valve 28. The reacted or effluent solution, now substantially de-ionized, proceeds thru a conduit 29 and is recirculated as by a pump 15 through conduit 30 returning to the organic buffer carrier solution reservoir 10 for recirculation.

The various conduit means including 18, 25, 26, 29, and 30 may be made of glass tubing or any such means conventionally used for such analytical apparatus; the only criteria being, of course, that they do not affect or are not affected by the solutions passing therethrough.

The conduit 25 may be formed by a conventional hollowed fitting and all of the conduit members are normally joined to the various chambers by conventional parts, normally made of a relatively inert material such as polytetrafluroethylene or nylon held together by conventional screwed compression fittings illustrated at 31, for example.

The reaction column containing the immobilized enzyme may be a conventional glass tubing column or one of a compatible plastic such as acrylic. Likewise, the remaining chambers of the apparatus may also be fabricated of any suitable material which is not affected or does not affect the solution passing therethrough.

The gel utilized for entrapping the enzyme is an specially prepared cross-linked acrylamide gel in which the cross-linking agent is normally N, N' - Methylenebisacrylamide having a very high ratio of an acryalmide to cross-linking agent, normally from about 45:1 to about 55:1. This high ratio gel yields a much improved enzyme entrapping latice in which leaching out of the urease molecules is greatly reduced. The preparation of the gel utilized in entrapping the enzyme and is described more fully in the co-pending application of Koch et al, Ser. No. 425,043 filed Dec. 14, 1973 (which is a division of Ser. No. 276,630 filed July 31, 1972, now abandoned) and assigned to the same assignee as the present application.

As described above, the buffered organic carrier solution must be one which in itself is essentially very low in electrical conductance and does not react with either the immobilized enzyme or any of the other solution species. The buffered carrier solution is normally in the form of a dilute aqueous solution adjusted to about pH 6–7. Some of the buffers successfully used include amion acid and similar compounds several of which are listed as follows:

Glycine
Tris (hydroyomethyl) aminomethane - maleate
Tris (hydroxymethyl) aminomethane
2-amino-2-methyl-1,3 propane diol The above or similar organic buffer systems provide a low conductance background forming a base reference point with which the increase of electrically active charge carriers can be compared to relate only to the amount of dissociated ammonium and carbonate ionic species obtained by the urea-water reaction. The carrier solution is maintained substantially free of inorganic ionic species by circulating the electrically-active reacted solution through the reclamation stage 14.

In the reclamation stage 14, the reclamation or regeneration of the buffered organic carrier solution can be achieved through any suitable chemical treatment such as by electro-dialysis, ion exchange membrane, ion exchange bed or by other suitable treatment of the solution. Any suitable conventional technique can be applied and these do not, in themselves, form a part of the present invention. It should be noted that the organic species and, in particular, the amino acid buffers have both + and − groups and thus are not affected by normal ion exchange techniques and this "iso-electric" phenomena can be used to advantage in reclaiming the organic buffer solution.

The capacity to recirculate the buffered organic solution and utilize it in the analysis many samples, of course, presents a distinct advantage over prior art batch-type systems which require the introduction of new carrier solution with the analysis of each sample which, in turn, leads to increased analysis costs. In accordance with the present invention, the requirement of cleaning or changing the reaction chamber associated with batch-type analytical techniques is also eliminated. The continual recirculation of the substantially de-ionized buffered organic carrier solution in accordance with the present invention assures that the system will be continuously cleansed between tests without the necessities of such procedures.

Another advantage of the instrument of the present invention lies in the fact that BUN determination may be made utilizing very small samples. A typical sample size is about 50 microliters. The volume of the various chambers in the system and the flowrate therethrough, which is controlled by the size of the conduits and the chambers, is designed so that the action which begins in the chamber 12 is substantially completed when the carrier solution containing the reacting species reaches the measurement chamber 13. Of course, the solution must be sufficiently dilute so that the ammonium carbonate produced by the reaction is in the substantially completely dissociated form when reaching chamber 13. The small sample size requirement aids in the reduction of the required size of both chambers 12 and 13.

As discussed briefly above, the electrical conductance of the substantially reactive solution in the chamber 13 eminating from an organic substantially iso-electric solution introduced before reaction, is related to the number of electrically active charge carriers produced by the urea-water (hydrolysic) reaction. This resulting increase in solution conductance can in turn be related to the urea concentration found in the sample of one of several convention methods.

The first of these methods, known as the direct reading method, is illustrated in the preferred embodiment and includes a pair of space electrodes 32 and 33 connected to a conductance measuring device, which may be a conventional AC impedance bridge 34, as by conductors 35 and 36. Because of the linear relationship between the number of electrically active charge carriers in the reacted solution and the solution conductance, the measured AC impedance may be used to calibrate the instrument based on known samples and the AC impedance obtained read directly as a percent urea in the biological sample used as by a meter or recording device shown at 37.

Other conventional read out methods which may be employed include a differential method, wherein a second conductance cell identical with the above-described conductance is placed in chamber 11 before the sample enters the column 12. By this method, the conductance readings are obtained both before the reaction and after the reaction. The difference between these signals then is directly related to the increase in ion species caused by the desire reaction and by utilizing conventional electronic means to obtain the difference in these signals, a meter or recording read out may easily be obtained.

Another conventional method of obtaining the conductance is to utilize a single conductance cell placed in the reaction chamber 13 to sense the rate of charge carrier production in that chamber during the reaction. The conductance cell is placed downstream of the point where the reaction is initiated i.e., the top of the column 13 so that the initial instantaneous jump does not interfere with the measurement.

In the second of the three above-mentioned methods the background solution conductance is less important as a measurement is taken of it for each test. In the third method, the rate of change is measured and again the background is of less importance.

It should also be noted that inasmuch as the rate of the enzyme-catalyzed reaction involved is somewhat temperature dependent, conventional temperature control means may be required in applications where temperature variations are like.

The embodiments of the invention in which an exclusive property or right is claimed are defined as follows:

1. A continuous method for determining the concentration of a component of interest in a sample wherein the detection of the concentration of charge carriers of an ionic indicating product species of an enzyme-catalyzed reaction is indicative of the concentration of said component of interest, said method comprising the steps of:
   combining said sample with a substantially ionically inactive carrier solution containing an organic buffer;
   flowing the combined solution through a quantity of an enzyme selected to catalyze the desired reaction, wherein said enzyme is immobilized in a manner which allows free contact between the solution components and the enzyme molecules occasioning substantially no loss of enzyme thereby;
   measuring the increase in conductance of said combined solution;
   generating an output indicative of the concentration of said component of interest;
   reclaiming said carrier solution after said enzyme catalyzed reaction by reducing the conductance of the reacted solution substantially to that existing before said reaction; and
   recycling said reclaimed carrier solution to be reused with subsequent samples.

2. The method of claim 1 wherein said output is generated by measuring the electrical conductance of said solution after said reaction.

3. The method of claim 1 wherein said output is generated by measuring the conductance of said solution both before and after said enzyme-catalyzed reaction, the difference therebetween being indicative of the concentration of said ionic indicating product species.

4. The method of claim 1 wherein said output is generated by measuring the rate of change of the electrical conduction of said solution during said reaction.

5. The method of claim 1 wherein said reclaiming of said carrier solution is achieved by substantially de-ionizing the reacted solution.

6. The method of claim 1 wherein said component of interest is urea and said immobilized enzyme is urease.

7. A continuous flow-through analytical apparatus for determining the concentration of a component of interest in a sample wherein the detection of the concentration of charge carriers of an ionic indicating product species of an enzyme-catalyzed reaction is indicative of the concentration of the component of interest, said apparatus comprising:
   a first chamber including an amount of an enzyme immobilized and disposed therein in a manner which allows free contact between said enzyme and a solution flowing therethrough,
   means for introducing a substantially ionically inactive, carrier solution containing an organic buffer into said chamber;
   means for introducing a sample into said carrier solution;
   sensor means for detecting the increase in said charge carriers in said combined solution;
   means for generating an output from said sensor related to the concentration of said species of interest;
   means for reclaiming said carrier solution after said reaction by reducing the conductance of said carrier solution substantially to that existing before said reaction; and
   means for recirculating said reclaimed solution.

8. The apparatus of claim 7 wherein said sensor means comprises a pair of electrical conductance measuring electrodes placed downstream of said first chamber.

9. The apparatus of claim 8 further comprising a second pair of conductance-measuring electrodes disposed in said apparatus at a point before said solution enters said first chamber.

10. The apparatus of claim 7 wherein said sensor means comprises a pair of conductance-measuring electrodes placed in said first chamber to measure the rate of production of said ionic charge carriers.

* * * * *